United States Patent
Collins et al.

(10) Patent No.: US 9,864,349 B2
(45) Date of Patent: Jan. 9, 2018

(54) MECHANISM FOR FACILITATING HYBRID SOLUTIONS FOR STAINING OF SPECIMENS

(71) Applicants: Mark Andrew Collins, Dripping Springs, TX (US); Mary Virginia Riley, Morrison, CO (US)

(72) Inventors: Mark Andrew Collins, Dripping Springs, TX (US); Mary Virginia Riley, Morrison, CO (US)

(73) Assignee: Piesi, Inc., Dripping Springs, TX (US)

( * ) Notice: Subject to any disclaimer, the term of this patent is extended or adjusted under 35 U.S.C. 154(b) by 633 days.

(21) Appl. No.: 14/139,753

(22) Filed: Dec. 23, 2013

(65) Prior Publication Data

US 2015/0177717 A1    Jun. 25, 2015

(51) Int. Cl.
  *G01N 1/30*   (2006.01)
  *G05B 15/02*  (2006.01)

(52) U.S. Cl.
  CPC ............... *G05B 15/02* (2013.01); *G01N 1/30* (2013.01)

(58) Field of Classification Search
  CPC .................................................. G01N 1/35
  See application file for complete search history.

(56) References Cited

U.S. PATENT DOCUMENTS

2004/0009098 A1* 1/2004 Torre-Bueno ............ G01N 1/31
                                                      422/63

* cited by examiner

*Primary Examiner* — Jyoti Nagpaul
(74) *Attorney, Agent, or Firm* — Blakely, Sokoloff, Taylor & Zafman LLP

(57) ABSTRACT

In accordance with embodiments, there are provided mechanisms and methods for facilitating hybrid solutions for staining of specimens according to one embodiment. In one embodiment and by way of example, a method includes receiving a request for a staining process for a specimen placed on a specimen container that is further placed within a process chamber, where the specimen includes a specimen needing a diagnosis. The method may further include reading or capturing process data relating to the specimen, where the process data includes at least one of basic information and customization instructions. The method may further include facilitating the staining process of the specimen based on the process data.

8 Claims, 8 Drawing Sheets

MECHANISM FOR FACILITATING HYBRID SOLUTIONS FOR STAINING OF SPECIMENS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

One or more implementations relate generally to specimen staining and, more specifically, to a mechanism for facilitating hybrid solutions for staining of specimens.

BACKGROUND

Conventional staining solutions are predominantly provided by either a "dipping and dunking" technique that immerse the slide repeatedly in a pool of chemicals for varying time periods, or a measured dose approach where a measured amount of chemicals are applied to the specimen through a dropper as a differentiating technique for tissue-based diagnosis, etc. However, these conventional solutions are power-consuming, time-consuming, inefficient, and costly as they require expensive equipment and reagents.

BRIEF DESCRIPTION OF THE DRAWINGS

In the following drawings like reference numbers are used to refer to like elements. Although the following figures depict various examples, one or more implementations are not limited to the examples depicted in the figures.

DETAILED DESCRIPTION

In the following description, numerous specific details are set forth. However, embodiments, as described herein, may be practiced without these specific details. In other instances, well-known circuits, structures and techniques have not been shown in details in order not to obscure the understanding of this description.

Embodiments provide for a mechanism for facilitating a hybrid solution for staining any number and type of specimens. The hybrid solution, in some embodiments, may provide for reducing the normal cost and power associated with a specimen staining process while simultaneously increasing its efficiency and speed. It is to be noted that embodiments are not limited to any particular type of specimen, such as a specimen may include (but not limited to) any number and types of chemical specimens, material specimens, tissue specimens, compounds, and other similar specimens undergoing chemical processes once placed onto a laboratory slide to analyze components and characteristics of said material. Further, for example, a medical/patient specimen may not be limited to humans and may include, for example, tissue samples from animals, plants, etc.

Embodiments may be applied to and used with any number and type of specimens including (but not limited to) anything from, for example, a medical specimen relating to a patient (e.g., a histological specimen including a microscopic anatomy of cells and/or tissues of humans, animals, plants, etc.) to a grutch from inside a well pipe to a sludge from a water treatment plant, or the like. For example, embodiments may be applied to and used with any number and type of medical specimens (such as a histological specimen, a biological specimen, etc.), physical specimens (such as a piece of a tire to test its durability, a piece of a computer to test for sustainable heat/temperature, etc.), mechanical specimens (such as a fragment of a machine to test its functionality, etc.), chemical specimens (such as a pharmaceutical specimen or a chemical compound for testing a drug, etc.), or the like. For example, if a chemical specimen or a physical specimen is being tested, then the user providing testing/customization information and/or monitoring the testing process may include a chemist or a physicist, respectively, as opposed to a doctor. It is contemplated that the user may include any number and type of other individuals of various qualifications, such as a laboratory technician, a nurse, a hospital/clinic administrator, a computer programmer, etc. However, for the sake of brevity, clarity, and ease of understanding, a specimen needing a diagnosis, such as a medical/patient specimen, is used as an example throughout this document but, as aforementioned, embodiment are not limited as such.

Figure 4A:
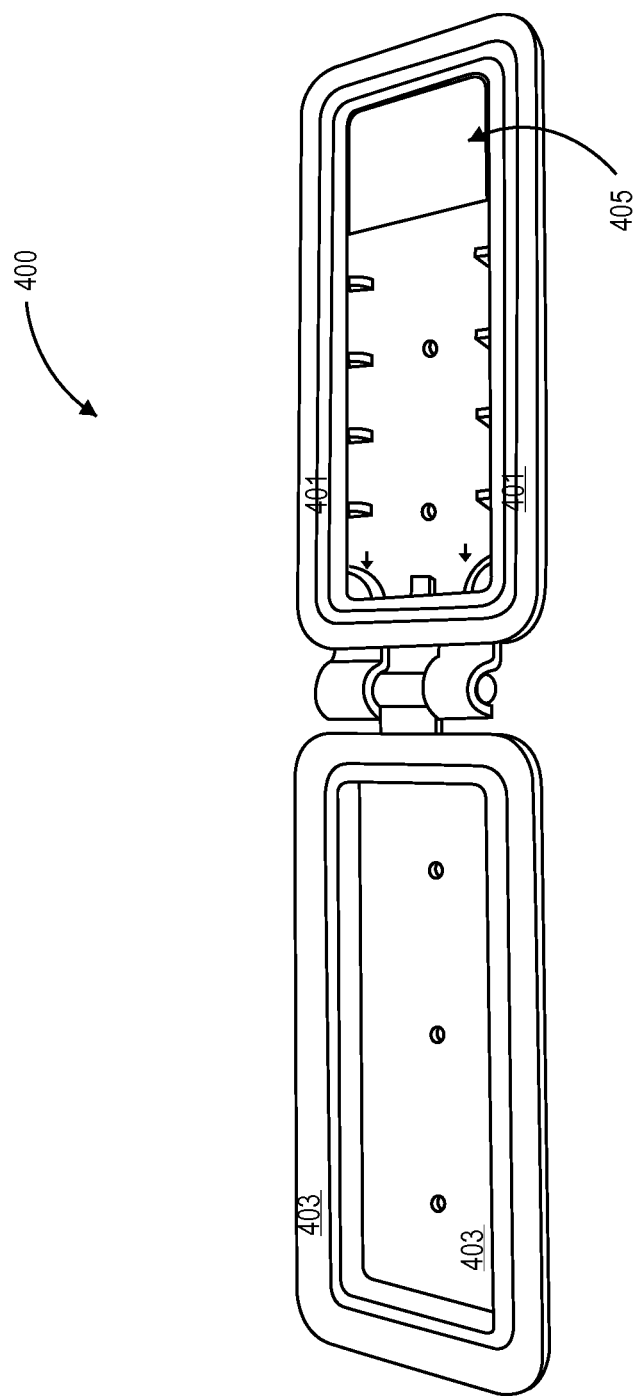
FIG. 4A illustrates a pressure chamber that encapsulates a slide that holds a specimen according to one embodiment.

Similarly, although a slide is illustrated in FIG. 4A and used as an example throughout this document for the sake of brevity, clarity, and ease of understanding, it is contemplated that embodiments are not limited to merely slides for holding specimens and that any number and type of containers made with a variety of materials (e.g., glass, plastic, etc.) may be used for holding any number and type of specimens. Embodiments may be applied to and used with any number and type of specimen containers including (but not limited to) slides, cassettes, test tubes, flasks, etc. It is to be further noted that depending on shapes, types, and quantities, etc., of specimens and/or specimen containers being used, various components and/or features of hybrid staining device 100 as illustrated with respect to FIG. 2 (and also with reference to FIGS. 1, 4B-4D, 5, etc.) may be accordingly and correspondingly altered, modified, added, removed, etc., to seamlessly and dynamically accommodate such specimens and/or specimen containers.

In one embodiment, the mechanism provides for aerosolized reagents through processes of osmosis and/or reverse osmosis absorption under hyper and hypobaric conditions to specimens undergoing staining processes. For example, a slide may be placed in a self-contained chamber, where each chamber is subjected to a specific chemical staining process as determined by, for example, a laboratory technician. These processes may be controlled and managed by an algorithm (e.g., software program or application) which may determine an order of, for example, chemical applications, an amount of chemical and duration of exposure of each chemical in the process, etc. Such chemicals may be introduced into the chamber through an atomizer, while the chamber is held at up to a number (e.g., 5) of atmospheres of pressure in order to improve absorption of the chemical at a faster rate. Further, once each process is completed, the chamber may be emptied of the chemicals under hyperbaric conditions and the next step in the process is initiated. This introduction and removal of chemicals may be repeated until the pre-programmed process for staining is completed. In some embodiments, any portion and type of the removed chemicals may be recycled if it is determined to be usable in order to achieve efficiency in the use of various materials, cost reduction, and elimination of any potential waste.

Throughout this document, terms like "logic", "component", "module", "framework", "engine", or the like, may be referenced interchangeably and include, by way of example, software, hardware, and/or any combination of software and hardware, such as firmware. Further, any use of a particular brand, word, term, phrase, name, acronym, or the like, such as "staining solution", "staining device", "Piesi™", "slide", "specimen", "immunohistochemistry (IHC)", "Hematoxylin and Eosin (H&E)", "dip and dunk", "routine staining", "special staining", etc., should not be read to limit embodiments to software or devices that carry that label in products or in literature external to this document. Further, for the sake of brevity, clarity, and ease of understanding, certain devices, techniques, methods, materials, chemicals, strainers, etc., may be referenced by name, such as IHC, H&E, routine staining, xylene, alcohol, eosin, clarifier, bluing, hematoxylin, etc.; however, it is to be noted that embodiments are not limited to these or other particular devices, techniques, methods, materials, etc., and that embodiments are applicable and compatible to and workable with all forms, manners, types, brands, and numbers of devices, techniques, methods, materials, chemicals, strainers, etc.

Figure 1:
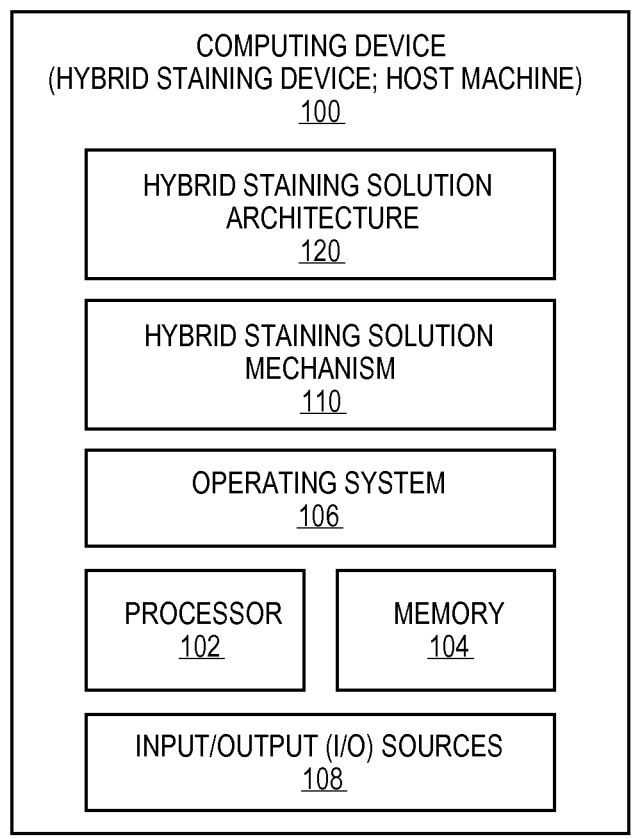
FIG. 1 illustrates a computing device hosting a hybrid staining solution mechanism according to one embodiment.

FIG. 1 illustrates a computing device 100 hosting a hybrid staining solution mechanism 110 according to one embodiment. Computing device 100 serves as a host machine for employing hybrid staining solution mechanism ("staining mechanism") 110 and hybrid staining solution architecture ("staining architecture") 120. Throughout the document, computing device 100 may be interchangeably referred to as "host machine", "hybrid staining device", "staining device", or simply "hybrid device". Computing device 100 may include large computing systems, such as server computers, desktop computers, etc., and may further include set-top boxes (e.g., Internet-based cable television set-top boxes, etc.), global positioning system (GPS)-based devices, etc. Computing device 100 may include mobile computing devices, such as cellular phones including smartphones (e.g., iPhone® by Apple®, BlackBerry® by Research in Motion®, etc.), personal digital assistants (PDAs), tablet computers (e.g., iPad® by Apple®, Galaxy 3® by Samsung®, etc.), laptop computers (e.g., notebook, netbook, Ultrabook, etc.), e-readers (e.g., Kindle® by Amazon®, Nook® by Barnes and Nobles®, etc.), etc.

Computing system 100 may serve as a staining device employing and hosting staining mechanism 110 and staining architecture 120 which may be accessed directly by a user or through another one or more computing devices (such as mobile computing devices, such as a smartphone, a tablet computer, a laptop computer, etc.) as will be further described with reference to FIG. 2. The term "user" may refer to an individual or a group of individuals (e.g., end-users, such as doctors, nurses, laboratory technicians, etc., administrative users, such as software programmers, system administrators, laboratory or office managers, etc.) who can access various features of staining mechanism 110 and staining architecture 120 by access computing device 100 via a software program or application (e.g., a downloaded or cloud-based application, such as a business application, a website, etc.) at the one or more computing devices accessible to the user.

Computing device 100 includes an operating system (OS) 106 serving as an interface between any hardware or physical resources of the computer device 100 and a user. Computing device 100 further includes one or more processors 102, memory devices 104, network devices, drivers, or the like, as well as input/output (I/O) sources 108, such as touchscreens, touch panels, touch pads, virtual or regular keyboards, virtual or regular mice, etc. It is to be noted that terms like "node", "computing node", "server", "server device", "cloud computer", "cloud server", "cloud server computer", "machine", "host machine", "device", "computing device", "computer", "computing system", and the like, may be used interchangeably throughout this document. It is to be further noted that terms like "application", "software application", "program", "software program", "package", and "software package" may be used interchangeably throughout this document. Similarly, terms like "job", "input", "request" and "message" may be used interchangeably throughout this document.

Figure 2:
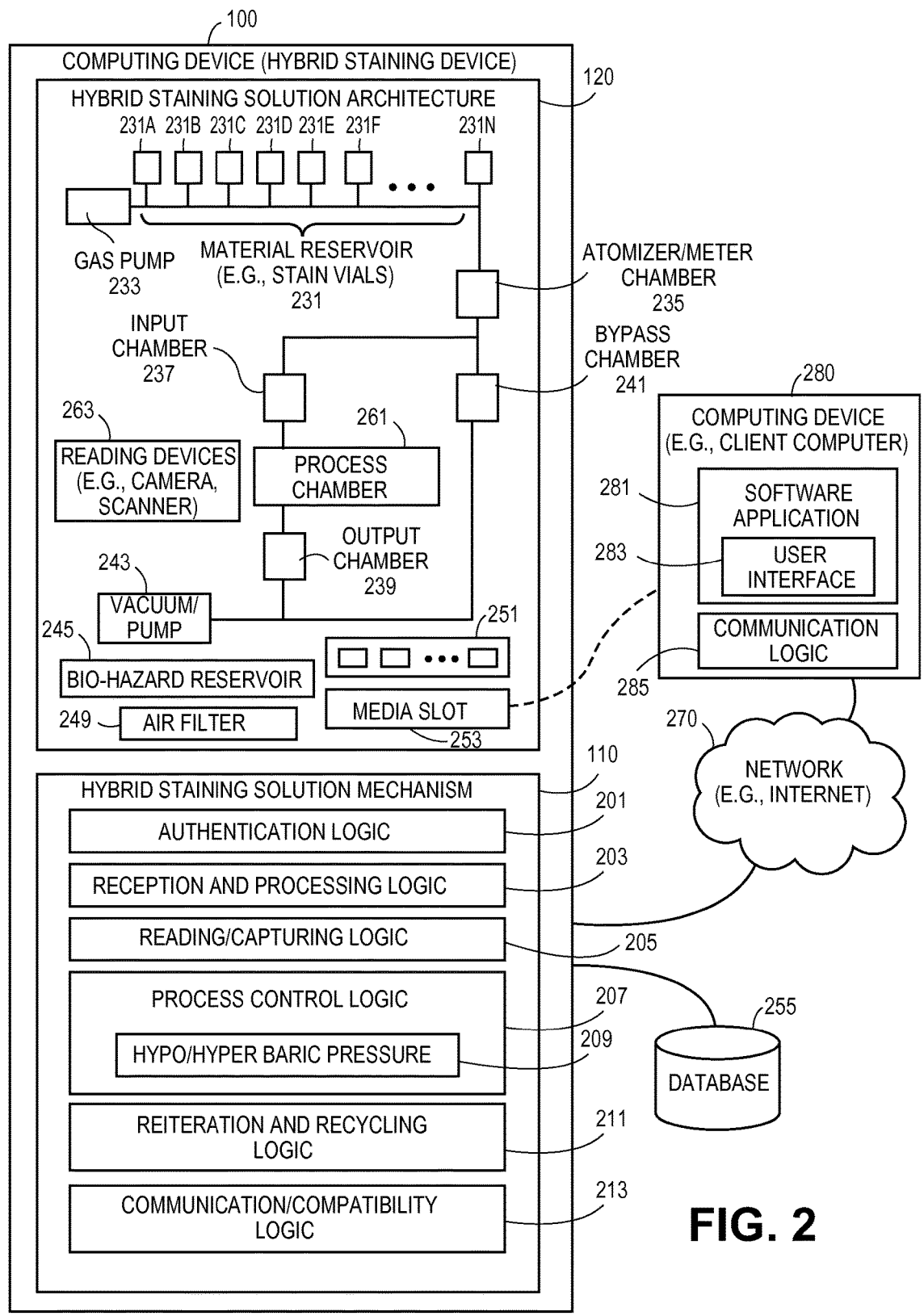
FIG. 2 illustrates a hybrid staining solution mechanism according to one embodiment.

FIG. 2 illustrates a hybrid staining solution mechanism 110 according to one embodiment. In one embodiment, staining mechanism 110 may include a number of components, such as: authentication logic 201; reception and processing logic 203; reading/capturing logic 205; process control logic 207 including hypo/hyper baric pressure module 209; reiteration and recycling logic 211; and communication/compatibility logic 213.

In one embodiment, staining mechanism 110 may be hosted at hybrid device 100 and further be in communication with one or more computing devices, such as computing device 280 (e.g., user-accessible client computing device, such as a desktop computer or a portable or mobile computer including a smartphone, a tablet computer, a laptop computer, etc.). Computing device 280 may be directly connected with hybrid device 100 via media slot 253 or over one or more networks, such as network 270 (such as a cloud network, the Internet, etc.). Staining mechanism 110 may further be in communication with one or more databases, such as database 255, and/or storage media (e.g., cloud storage) having stored thereon instructions, data, resources, policies, raw files, distributed file system, etc.

Computing device 280 may include a client computing device hosting a client-based software application 281 which may be deployed or downloaded on computing device 280 or accessed via one or more networks (e.g., cloud network), such as network 270, that provides one or more users interfaces, such as user interface 283, to facilitate the user to access and/or use staining mechanism 110 and staining architecture 120. User interface 283 may include, but is not limited to, one or more of a web user interface (WUI), a graphical user interface (GUI), and a touchscreen, etc. It is contemplated that computing device 280 may further include communication logic 285, audio/visual devices (e.g., cameras, microphones, speakers, etc.), sensors (e.g., temperature sensor, biometric sensor, fingerprint sensor, etc.), scanners (e.g., barcode scanner, patient information reader, etc.), etc., and may further include memory, local storage devices, databases, etc., for storing and caching data.

In one embodiment, staining architecture 120 include one or more component, such as: material reservoir 230 having any number and type of stain vials 231A-231N; gas pump 233; atomizer/meter chamber 235; input chamber 237; output chamber 239; bypass chamber 241; vacuum/pump 243; bio-hazard reservoir 245; air filter 249; active process statistics table displayer ("statistics displayer") 251; media slot 253; reading devices 263; and stainer process chamber 261. Like stain vials 231A-231N, process chambers are not limited to any particular size or number, such as staining device 100 having up to 33 process chambers with each chamber sufficiently sized to hold a specimen slide as will be illustrated with regard to FIG. 4A; however, for brevity and clarity, a single process chamber 261 is illustrated and discussed here. For example and in some embodiments, hybrid device 100 may have 33 process chambers as will be further illustrated with reference to FIGS. 4B-4D.

To initiate a staining process, a slide having the ability and space to hold a specimen may be marked with a printed label, including a barcode, denoting relevant information, such as patient name, doctor name, hospital name, stain type, reason for staining, etc. The slide may be the same or similar to the one illustrated with respect to FIG. 4A. The specimen may then be placed onto the slide and the slide may then be placed into process chamber 261. In one embodiment, the slide label or the barcode embedded in or pasted on the label may not only include basic information, but may also include customization instructions which may be easily extracted or read by one or more reading or capturing devices 263 (e.g., camera, scanner, barcode reader, etc.) of process chamber 261. For example, one or more reading devices 263 may be planted at the bottom side of the lid of process chamber 261 from where the customization instructions may be read or captured. Such customization information may be provided to supplement the basic information, where the customization information may include instruction regarding one or more preferred or required chemicals to be extracted from material reservoir 231 to be used for the staining process, an amount of pressure or changing pressure to be applied within the process chamber 261, a time limit to be applied to the staining process, one or more changing colors or forms of the specimen to be noted or recorded, and the like.

For example, reading device 263 may include a camera to capture one or more pictures of the specimen along with any customization instructions and other relevant basic information provided by the user. Similarly, reading device 263 may include a scanner and/or a barcode reader to scan or read the customization instructions and the relevant basic information. Once captured, the customization and basic information along with any pictures may be used to perform a customized staining process on the specimen within process chamber 261 as facilitated by various components of staining architecture 120 and staining mechanism 110.

In addition or as an alternative to providing customization instructions and basic information via the label or barcode on the slide, in one embodiment, the user (e.g., doctor, laboratory technician, nurse, etc.) may choose to directly program the staining process feeding in the relevant information or instructions through software application 281, visa user interface 283, at client computing device 280. As aforementioned, computing device 280 (such as a smartphone, a tablet computer, a laptop computer, etc.) may be directly placed in or connected through media slot 283 and/or over network 270. These user-inputted customization instructions and relevant basic information may be used by one or more processing devices, such as processor 102 of FIG. 1, to automatically program the staining process to be customized as requested by the user.

In one embodiment, authentication logic 201 may be used to identify and authenticate the user, such as via user identification (userID), password, fingerprints, etc., and/or any number and type of devices, such as computing device 280, such as via unique device identification, Internet Protocol (IP), etc. Once the identification and authentication of the user and/or computing device 280 is performed, any information provided by the user, whether entered through software application 281 or through the label/barcode on the slide, may then be received and processed at reception and processing logic 203. In one embodiment, reception and processing logic 203 may sort and filter through all the data, including any basic information relating to one or more of patient, doctor, hospital, disease, specimen, technician, research protocol, etc., and/or any customization instructions (e.g., type and amount of chemical, process time period, level of applied pressure, etc.) so that correct and necessary information may be extracted and used to properly customize and facilitate the staining process.

In one embodiment, reception and processing logic 203 may work with reading/capturing logic 205 to ensure any customization instructions and/or basic information are properly read (such as via a scanner of reading devices 263) and/or any pictures of the specimen and/or other relevant data or description are properly captured (such as via a camera of reading device 263). Once the reading/capturing process is completed, the customization parameters for the staining process are set, such as based on the user/doctor's preferences, and are then forwarded on to process control logic 207 for further processing.

In one embodiment, upon receiving the customization parameters, process control logic 207 facilitates various components, such as vacuum/pump 243, gas pump 233, etc., of staining architecture 120 to perform their respective tasks. For example, based on the customization parameters, vacuum/pump 243 may begin to expand and/or contract to control, such as reduce and/or increase, the pressure within process chamber 261, such as per the customization parameters, the pressure inside process chamber 261 may be reduced below the normal atmospheric pressure causing the specimen walls to expand. Upon reaching the appropriate pressure, process control logic 207 may then facilitate other components, such as gas pump 233, material reservoir 231, atomizer/meter chamber 235, etc., to perform their tasks. For example, per the customization parameters, the right amount of gas may be pumped through gas pump 233, such as a sufficient amount of nitrogen may be pumped to change the permeability of the specimen cell.

In one embodiment, process control logic 207 may then facilitate the right amount and type of formulation (e.g., chemicals, materials, etc.) be extracted from one or more of stain vials 231A-231N of material reservoir 231. For example, one or more formulations in their proper corresponding amounts, as prescribed by the customization parameters (that may be based on or include doctor preferences, staining protocols, technician instructions, research protocol, etc.), may be extracted from one or more stain vials 231A-231N and yet again as prescribed by the customization parameters (that may be based on or include doctor preferences, staining protocols, technician instructions, research protocol, etc.), a sufficient amount of each of the extracted amounts of the one or more formulations may be properly adjusted or metered by atomizer/meter chamber 235 so that a metered amount of each of the extracted formulation may be transformed into vapor state. These vapor formulations are then inputted, via input chamber 237, into process chamber 261. For example and in some embodiments, stain vials 231A-231N may include, but is not limited to the following formulations, such as vial 231A having hematoxylin, vial 231B having water, vial 231C having clarifier, vial 231D having bluing, vial 231E having eosin, vial 231F having alcohol, and vial 231N having xylene. It is contemplated that embodiments are not limited to the aforementioned and that any other types of formulations may be employed and used, whereas any of the aforementioned formulations may be removed and not used.

In one embodiment, process control logic 207 triggers hypo/hyper baric pressure module 209 to facilitate osmosis and/or reverse osmosis process on the specimen within the process chamber 261. For example, using vacuum/pump 243, the pressure within the pressure chamber containing the slide having the specimen may be increased within process chamber 261 based on the customization parameters, such as stain types, patient or specimen protocols, doctor preferences, technician instructions, research protocol, etc., to cause osmosis or osmotic process to allow the formulations (e.g., materials, chemicals, etc.) to more easily cross cell wall boundaries and be uniformly absorbed through the cell walls of the specimen. Further, using vacuum/pump 243, the pressure inside process chamber 261 may continue to increase above the normal atmospheric pressure based on the customization parameters, such as stain types, protocols, doctor preferences, technician instructions, research protocol, etc., until the stain absorption becomes uniform.

It is contemplated that osmosis refers to a spontaneous movement of solvent molecules through a partially permeable membrane into a region of higher solute concentration in the direction that tends to equalize the solute concentrations on the two sides of the membrane. Reverse osmosis refers to a separation process that uses pressure to force a solvent through a semi-permeable membrane that retains the solute on one side and allows the pure solvent to pass to the other side. In other words, reverse osmosis refers to a process of forcing a solvent from a region of high solute concentration through a membrane to a region of low solute concentration by applying a pressure in excess of the osmotic pressure.

Using hypo/hyper baric pressure induces the osmosis and reverse osmosis processes that induce the formulations to penetrate through the cell wall of the specimen to properly reach the specimens to provide a better concentration and/or penetration of chemicals into the specimen cells. For example and in one embodiment, since each cell in the specimen undergoes an osmotic process, there is a better concentration of the stain and it is significantly more even distribution of the stain across the entire specimen instead of it being typically confined to the outer edges of the specimen. Further, using the hypo/hyper baric pressure to induce the osmosis/reverse osmosis process-based penetration of the formulations, a significant reduction in the use of chemicals, reagents, enzymes, etc., may be achieved, such as when preparing the specimen for diagnostic purposes. For example, since the specimen undergoes the osmotic process, it may take significantly less actual staining compound to produce the same result. Moreover, since the use of a hypo/hyperbaric pressure to induce the osmosis process does not involve the conventional heating/cooling of the specimen cells, there is less potential for damage to the specimen itself, which may provide new insights to existing specimens not seen before since there is no alteration and/or adulteration of the specimen in the absence of the convention heating/cooling cycle that is typically used for some forms of the staining process.

Furthermore, the velocity of the process is significantly improved by coercing the specimen through a negative and positive pressure osmotic process which causes the cell walls of the specimen to become more penetrable with the staining agent at a much faster rate and in a very short amount of time. Further, by reducing the overall staining time, the diagnostic turn-around time is also significantly improved. This novel use of osmosis/reverse osmosis process is vastly distinct from the current routines and IHC staining processes that are inefficient and time consuming as they rely on either a "dip and dunk" immersion of the specimen or heating/cooling of a specimen for a period of time to get it to expand and contract in order to absorb the chemicals or reagents acting upon it and then dripping the stain onto the specimen to make it easier to stain the pathogen.

In one embodiment, exposure to chemicals is strictly controlled due to pre-programmed methodologies where a user, such as a doctor or a laboratory technician, can subject staining mechanism 110 and staining architecture 120 to function in accordance a program that is introduced or inputted through user application 281 at client computing device 280. Further, the cost of the equipment is also significantly reduced due to the stationary nature of the process. For example and in one embodiment, there remains no need for transportation of the slide from chemical to chemical or chemical delivery mechanism to the slide, since each chemical is introduced from its corresponding stain vial 231A-231N directly into its corresponding process chamber, such as process chamber 261, without having to move the chambers or the chemical delivery mechanism. Additionally, it is contemplated that the introduction of chemicals under hyperbaric and hypobaric conditions eliminates the need for heating of specimens and thus reducing the conventionally-needed complicated electrical heating and cooling components and significantly reducing the power consumption. Further, due to the reduced instrumentation for the process, the footprint of the equipment is also significantly reduced which improves the laboratory space utilization as significant amount of laboratory space may be left to be used for other purposes. Since the equipment is built on individual components, the maintenance of the units is also significantly enhanced. In some embodiments, chemicals may not be re-used for multiple specimens which reduces the potential conventional cross-contamination of specimens and also the risk of cross-contamination of chemicals due to residual chemicals from prior chemical exposure processes in conventional techniques, such as the dip and dunk method.

Referring back to the process at process chamber 261, once the pressure within process chamber 261 is reduce to the normal atmospheric pressure, any remaining formulations are removed from process chamber 261, via output chamber 239 and as facilitated by process control logic 207, in anticipation of a next formulation to be introduced into process chamber 261. As aforementioned, for each process, a new set of customization parameters and other protocols, such as patient information, disease information, specimen data, doctor's preferences, technician instructions, research protocol, etc., may be inputted via user interface 283 of software application 281 at client computing device 280 and/or provided through the label or barcode on the specimen slide. In one embodiment, at later time, chemicals may be filtered, reconstituted, or used in some other fashion or form.

In one embodiment, reiteration and recycling logic 211 may be used to determine whether the same specimen or set of specimens needs to go through another staining process and a new specimen or set of specimens needs be introduced to go through its own staining process according to its corresponding customization parameters. Any of the formulations that are not to be used or upon exhaustion of all formulations, the remaining materials may be properly disposed with, as facilitated by reiteration and recycling logic 211, by having them placed in bio-hazard reservoir 245. In another embodiment, bio-hazard reservoir 245 may be subdivided into one or more reservoirs to isolate various different chemicals that may then be recycled. The subsequent disposal of the materials from bio-hazard reservoir 245 may be performed in a manner that is cost-efficient, time-efficient, and environmentally friendly.

In one embodiment, staining architecture 120 may include air filter 249 to filter air throughout the staining process to keep the air clean from any foreign particles, dust, etc., so as not to negatively affect the staining process. Further, in one embodiment, staining architecture 120 may further include statistics displayer 251 to continuously display the statistics or status of the staining process, such as the step number in the process, time consumed on the current step, time consumed on the entire process, remaining number of steps, remaining time, or the like. This information or data may be displayed in any form, such as in table or text, etc., on a display screen of hybrid device 100 and/or communicated to client computing device 280 to be displayed at its display screen.

Communication logic 285 of computing device 280 may be similar to or the same as communication/compatibility logic 213 and may be used to facilitate communication with staining mechanism 110 and staining architecture 120 at hybrid device 100 over one or more networks, such as network 270. Further, logic 285, 213 may be arranged or configured to use any one or more of communication technologies, such as wireless or wired communications and relevant protocols (e.g., Wi-Fi®, WiMAX, Ethernet, etc.), to facilitate communication over one or more networks, such as network 270 (e.g., Internet, intranet, cloud network, proximity network (e.g., Bluetooth, etc.)). Database 255 may include any number and type of devices or mediums (such as data storage devices, hard drives, solid-state drives, hard disks, memory cards or devices, memory circuits, etc.) for short-time and/or long-term storage of data (e.g., patient information, customization parameters, process protocols, etc.), policies, resources, software programs or instructions, etc.

Communication/compatibility logic 213 may be used to facilitate dynamic communication and compatibility between various computing devices, such as hybrid device 100 and client computing device 280 (e.g., client computing device, such as a mobile computing device, a desktop computer, etc.), storage devices, databases and/or data sources, such as database 255, networks, such as network 270 (e.g., cloud network, the Internet, intranet, cellular network, proximity networks, such as Bluetooth, Bluetooth low energy (BLE), Bluetooth Smart, Wi-Fi proximity, Radio Frequency Identification (RFID), Near Field Communication (NFC), Body Area Network (BAN), etc.), connectivity and location management techniques, software applications/websites, (e.g., social and/or business networking websites, such as Facebook®, LinkedIn®, Google+®, Twitter®, etc., business applications, games and other entertainment applications, etc.), programming languages, etc., while ensuring compatibility with changing technologies, parameters, protocols, standards, etc.

Although one or more examples may be discussed throughout this document for brevity, clarity, and ease of understanding, it is contemplated that embodiments are not limited to any particular number and type of specimen, formulation materials, forms of access to resources or devices, users, network or authentication protocols or processes, or the like. For example, embodiments are not limited to any particular network security infrastructures or protocols (e.g., single-sign-on (SSO) infrastructures and protocols) and may be compatible with any number and type of network security infrastructures and protocols, such as security assertion markup language (SAML), OAuth, Kerberos, etc.

It is contemplated that any number and type of components may be added to and/or removed from any one or more of staining mechanism 110 and staining architecture 120 to facilitate various embodiments including adding, removing, and/or enhancing certain features. For brevity, clarity, and ease of understanding of staining mechanism 110 and staining architecture 120, many of the standard and/or known components, such as those of a computing device, are not shown or discussed here. It is contemplated that embodiments, as described herein, are not limited to any particular technology, topology, system, architecture, and/or standard and are dynamic enough to adopt and adapt to any future changes.

Figure 3:
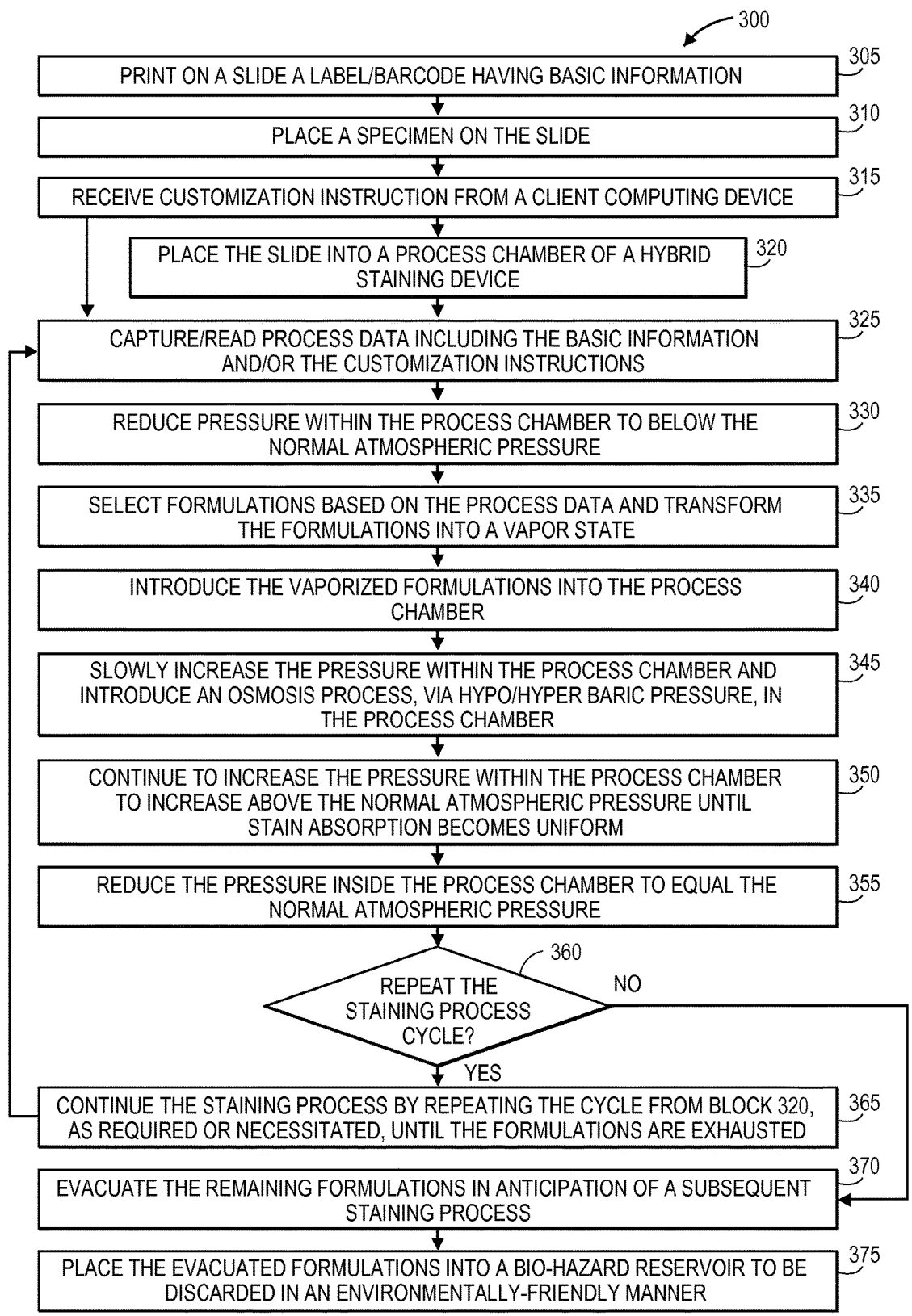
FIG. 3 illustrates a method for facilitating a hybrid staining solution for specimens initiating a hypo/hyper baric pressure condition to induce osmosis/reverse osmosis at a hybrid staining device according to one embodiment.

FIG. 3 illustrates a method 300 for facilitating a hybrid staining solution for specimens using a process for osmosis/reverse osmosis at a hybrid staining device according to one embodiment. Method 300 may be performed by processing logic that may comprise hardware (e.g., circuitry, dedicated logic, programmable logic, etc.), software (such as instructions run on a processing device), or a combination thereof. In one embodiment, method 300 may be performed by staining mechanism 110 and staining architecture 120 of FIG. 1. The processes of method 300 are illustrated in linear sequences for brevity and clarity in presentation; however, it is contemplated that any number of them can be performed in parallel, asynchronously, or in different orders.

For the sake of brevity, many of the details described with reference to FIG. 2 are not repeated here. It is to be noted yet again that as with FIG. 2, even though a single process chamber, such as process chamber 261 of FIG. 2, are discussed here, hybrid device 100 is not limited to any particular number or size of process chambers as illustrated with reference to FIGS. 4B-4D where hybrid device 100 is shown to have up to 33 process chambers with each process chamber having an audio/visual/scanning/reading devices, such as a camera, a microphone, a scanner, a barcode reader, etc.

Method 300 begins at block 305 with a slide capable of holding a specimen is printed with a label or have a barcode placed on it having some basic information relevant to the specimen, such as patient name and other data, type of disease, stain type, doctor information, research project, technician or laboratory information etc. At block 310, the specimen is placed on the slide.

In one embodiment, at block 315, along with the aforementioned basic information, additional customization instructions may be provided a user (e.g., patient's doctor, nurse, laboratory technician, research project, or laboratory information etc.) via a client computing device (e.g., desktop computer, laptop computer, tablet computer, smartphone, etc.) by directly connecting the client computing device to the hybrid device via a media slot, such as media slot 253 of FIG. 2, or communicating with the hybrid device over a network, such as the Internet, a cloud network, a proximity computer, etc. The user may input the customization instructions using via a user interface of a software application at the client computing device. As discussed with reference to FIG. 2, customization instructions may include doctor or technician preferences regarding the staining process, such as which materials, chemicals, enzymes, etc., to use for each specimen and for how long the process ought to continue for each specimen, what changes to detect in each specimen, such as via the camera in the process chamber, etc. It is contemplated that these customization instructions may be based on any number and type of factors, such as the type of specimen, type of disease, patient history, material type etc.

At block 320, the slide having the specimen is placed in one of the several process chambers of hybrid device 100 having staining mechanism 110 and staining architecture 120 as illustrated with reference to FIG. 2. At block 325, using one of the audio/visual/scanning/reading devices of the process chamber (e.g., installed under the top lid of the process chamber), such as a camera or a barcode scanner, the basic information and/or the customization instructions may be captured or read so that the subsequent staining process on the specimen may be performed based on the basic information and/or the customization instructions.

At block 330, using process control logic 207 and vacuum/pump 243 of FIG. 2, the pressure inside the process chamber is reduced below the normal atmospheric pressure causing the specimen walls to expand. At block 335, based on the basic information and/or the customization instructions, formulations of materials, chemicals, enzymes, etc., are selected from one or more stain vials at a material reservoir, such as material reservoir 231 of FIG. 2, where metered amounts of the selected formulations is transformed into vapor state. At block 340, the vaporized formulations are introduced into the process chamber.

At block 345, the pressure within the process chamber is slowly increased, based on the basic information and/or customization instructions, to cause an osmotic process, via hypo/hyper baric pressure module 209 of FIG. 2, to allow the formulations to easily cross the cell wall boundaries and be uniformly absorbed into the specimen cell walls. At block 350, based on the basic information and/or customization instructions, the pressure inside the process chamber continues to increase above the normal atmospheric pressure until the stain absorption becomes uniform. At block 355, the pressure within the process chamber is reduced to equal the normal atmospheric pressure.

At block 360, a determination is made as to whether the staining process needs to be reiterated or repeated for the current specimen with one or more of the same formulations, such as based on the basic information and/or customization instructions. If yes, at block 365, the staining process cycle is repeated, as required or necessitated, such as until all or any of the relevant formulations are exhausted and/or as specified in the basic information and/or customization instructions. At block 370, if the staining process is not to be repeated for this specimen and/or using any of the currently-selected formulations, the remaining formulations are evacuated in anticipation of another subsequent staining process using another specimen or set of specimen and/or other formulations. At block 375, any remaining formulations are removed and temporarily stored in a biohazard compartment or reservoir, such as biohazard reservoir(s) 245 of FIG. 2, until the formulations are carefully removed from the biohazard reservoir to be discarded in a manner that is cost-efficient, time-efficient, and environmentally friendly.

FIG. 4A illustrates a pressure chamber that houses a slide 400 to hold a specimen according to one embodiment. Slide 400 may be made of any material, such as plastic, and include two flaps 401, 403 to serve as lids to include a specimen within them. As illustrated, one of the flaps, such as flap 401, may include a label 405, having may be a barcode, to include basic information about the specimen, the patient, the doctor, the material, research project, technician or laboratory information etc.

Figure 4B:
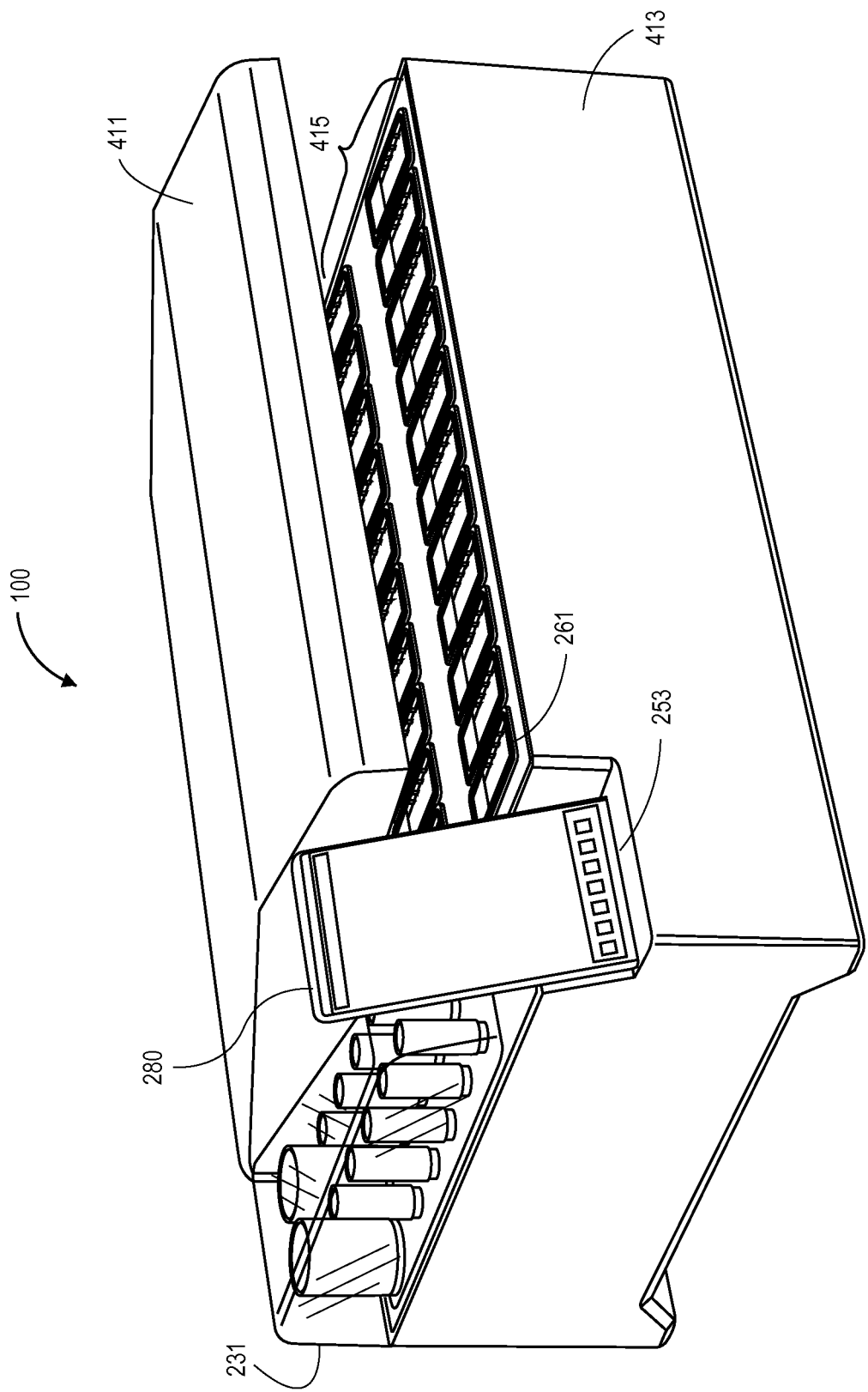
FIGS. 4B-4D illustrate various view of a hybrid staining device according to one embodiment.

FIG. 4B illustrates a hybrid staining device 100 according to one embodiment. As illustrated computing hybrid staining device 100 includes top chamber 411 and bottom chamber or bottom chamber 413. Hybrid device 100 is further shown to include a set of process chambers 415 that includes any number of individual process chambers, including process chamber 261 of FIG. 2, that are arranged in a number of rows, such as 3 rows with each row having 11 process chambers for a total of 33 process chambers. As illustrated, hybrid device 100 further provides one or more media slots, such as media slot 253, to hold one or more client computing devices, such as client computing device 280. Hybrid device 100 further shown to include material reservoir 231 having stain vials 231A-231N of FIG. 2 to hold materials, chemicals, enzymes, water, alcohol, etc., to be used for the staining process.

Further, in one embodiment, hybrid device 100 includes staining mechanism 110 and staining architecture 120 where various components of staining architecture 120 may be strategically placed throughout hybrid device. For example, air filter 249 and bio-hazard reservoir 245 may be placed within bottom chamber 413 so, for example, any waste from the formulations is easily gathered in bio-hazard reservoir 245 at the bottom of hybrid device 100. Similarly, any audio/visual devices and/or scanners/readers may be placed at the bottom portion of top chamber 411 so they are strategically faced down to obtain or capture the relevant information from the label/barcode of the slide, such as label 405 of slide 400, via a scanner/reader and/or from the specimen itself, such as by taking pictures using a camera. It is contemplated that the bottom portion of top chamber 411 may include any number of audio/visual devices and/or scanners/readers as may be desired or necessitated; for example, if there are 33 process chambers 415, there may be 33 cameras and/or scanners strategically placed at the bottom of top chamber 411 such that when top chamber 411 is closed over bottom chamber 413, each process chamber of process chambers 415 directly corresponds to at least at least one camera/scanner/reader.

Figure 4C:
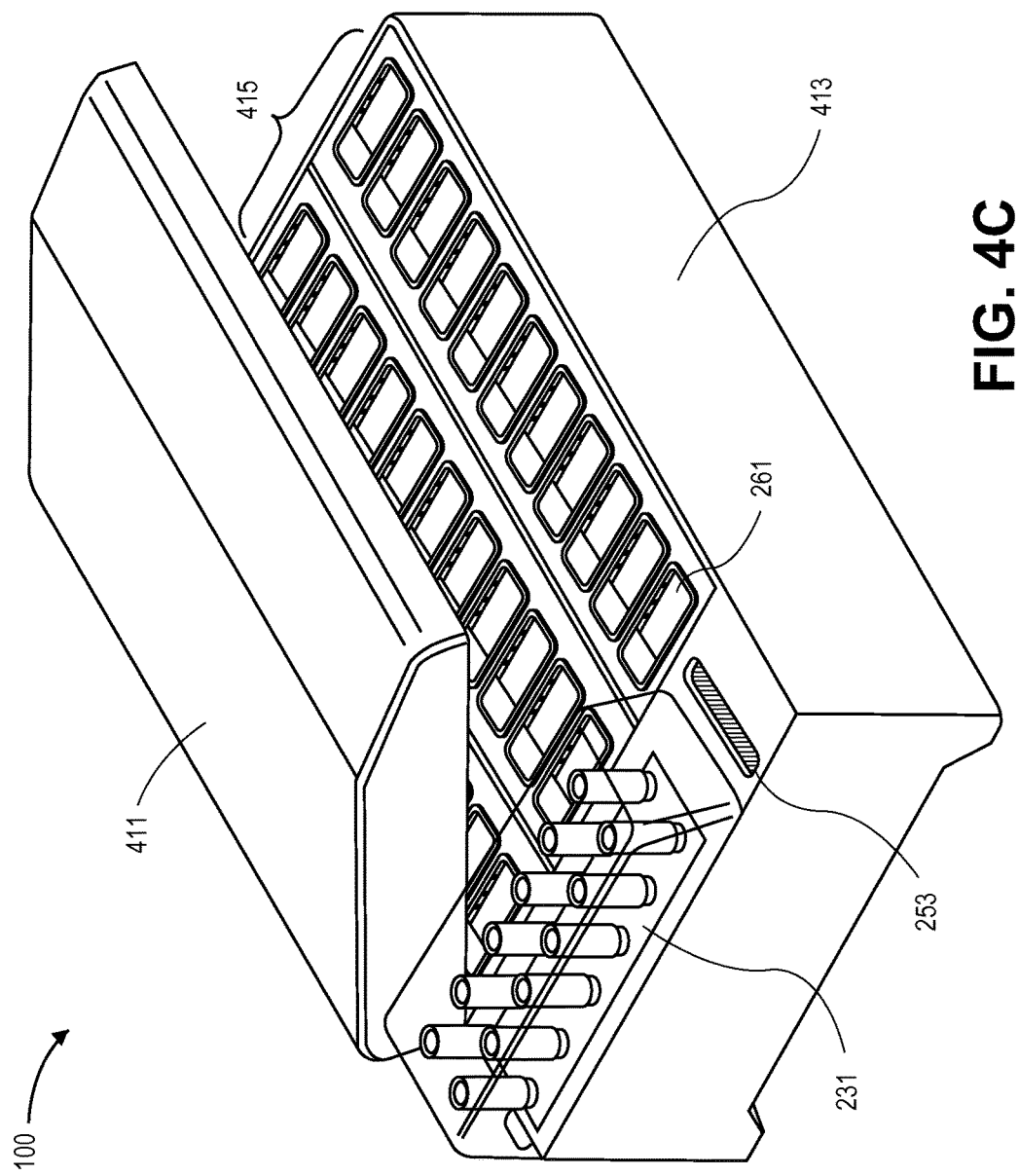

FIG. 4C illustrates another view of a hybrid staining device 100 according to one embodiment. As with FIG. 4B, Hybrid device 100 is shown to include top chamber 411, bottom chamber 413, process chambers 415 including process chamber 261 of FIG. 2, material reservoir 231 having stain vials 231A-231N of FIG. 2, and one or more media slots, such as media slot 253.

Figure 4D:
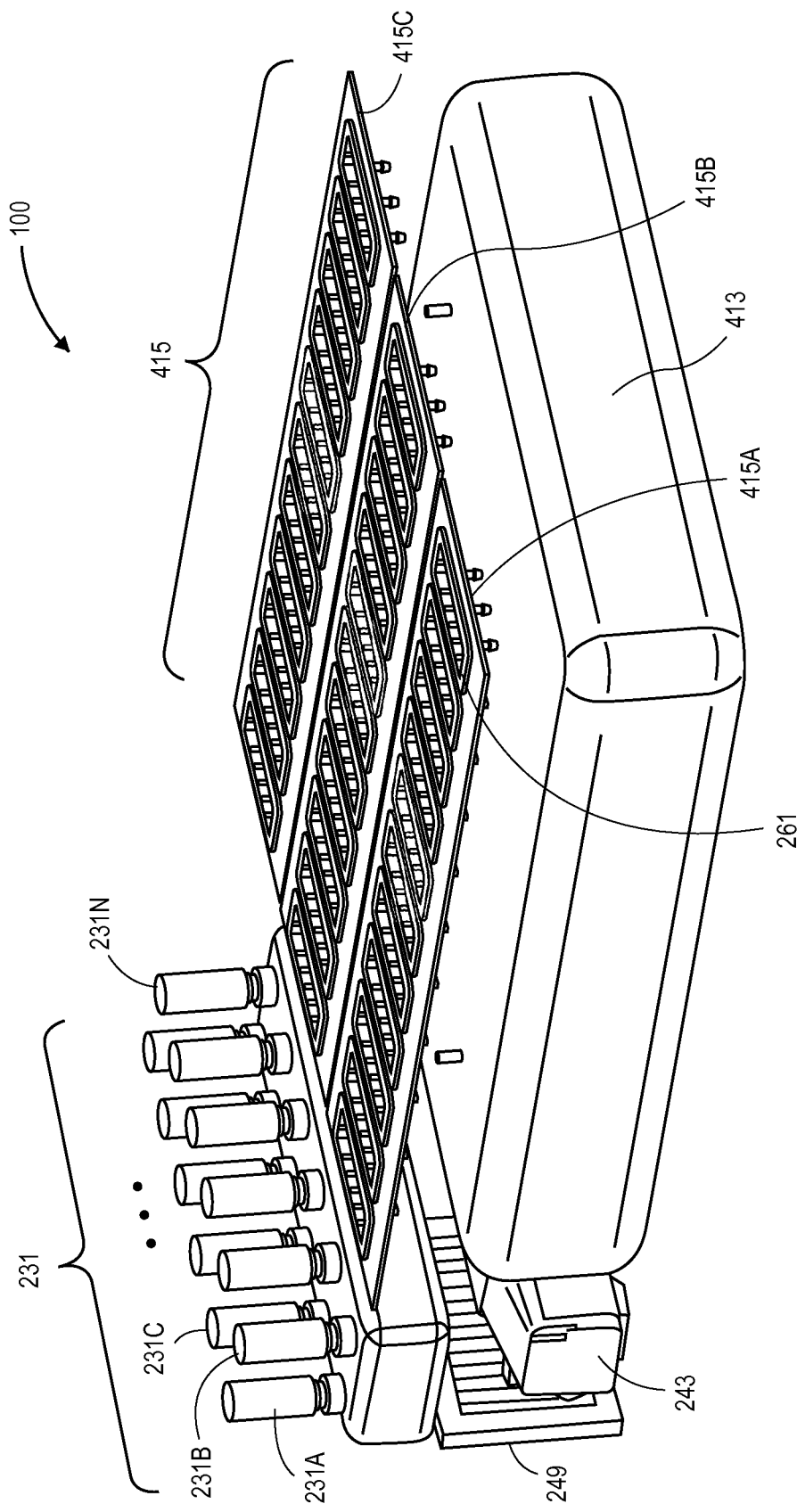

FIG. 4D illustrates a stripped view of a hybrid staining device 100 according to one embodiment. As shown in reference to FIGS. 4A-4B, hybrid device 100 includes material reservoir 231 having any number and type of stain vials, such as stain vials 231A-231N of FIG. 2. In the illustrated embodiment, top chamber 411 of hybrid device 100 has been removed to show all the process chambers 415. As illustrated, in one embodiment, 33 process chambers 415 may be divided into three rows process chambers 415A, 415B, 415C, where each row 415A, 415B, 415C is shown to include 11 process chambers each, such as process chamber 261 of FIG. 2 is shown to be included in row 415A. However, as previously stated, hybrid device 100 is not limited to any number, type, and/or size of process chambers and that merely be used as an example and for the sake of brevity and clarity, this illustration of FIG. 4D is shown to provide 33 process chambers 415 being arranged in three process chamber rows 415A, 415B, 415C with each row 415A, 415B, 415C having 11 process chambers.

Figure 5:
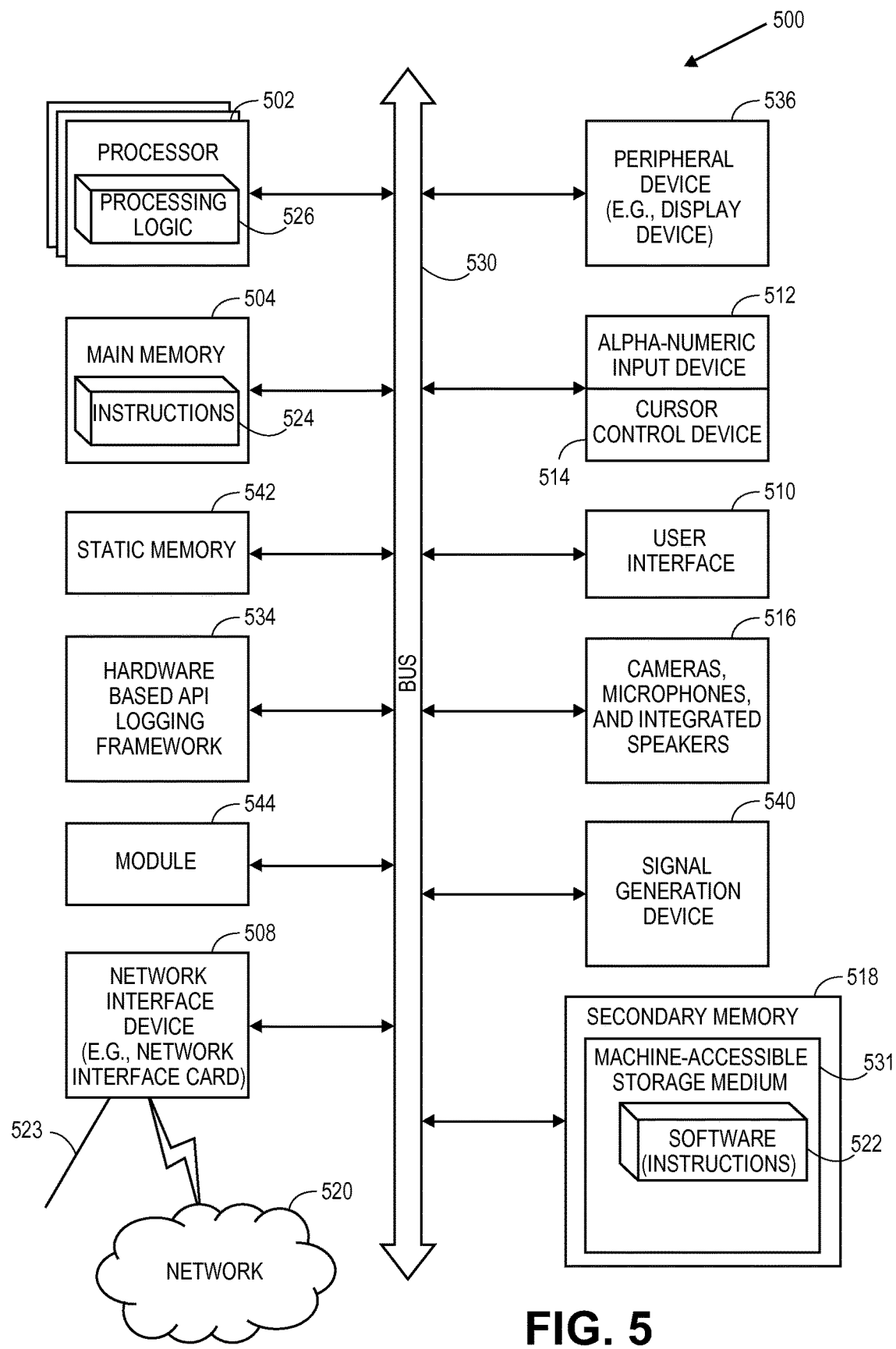
FIG. 5 illustrates a computer system according to one embodiment.

FIG. 5 illustrates a diagrammatic representation of a machine 500 in the exemplary form of a computer system, in accordance with one embodiment, within which a set of instructions, for causing the machine 500 to perform any one or more of the methodologies discussed herein, may be executed. Machine 500 may be the same as or similar to computing device 100 and computing device 280 of FIG. 1 and FIG. 2, respectively. In alternative embodiments, machine 100 may be connected (e.g., networked) to other machines either directly, such as via media slot 253 of FIG. 2, or over a network (such as hybrid device 100 connected with client computing device 280 over network 270 of FIG. 2), such as a cloud-based network, a Local Area Network (LAN), a Wide Area Network (WAN), a Metropolitan Area Network (MAN), a Personal Area Network (PAN), an intranet, an extranet, or the Internet. The machine may operate in the capacity of a server or a client machine in a client-server network environment, or as a peer machine in a peer-to-peer (or distributed) network environment or as a server or series of servers within an on-demand service environment, including an on-demand environment providing multi-tenant database storage services. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 500 includes one or more processors 502, a main memory 504 (e.g., read-only memory (ROM), flash memory, dynamic random access memory (DRAM) such as synchronous DRAM (SDRAM) or Rambus DRAM (RDRAM), etc., static memory 542, such as flash memory, static random access memory (SRAM), volatile but high-data rate RAM, etc.), and a secondary memory 518 (e.g., a persistent storage device including hard disk drives and persistent multi-tenant data base implementations), which communicate with each other via a bus 530. Main memory 504 includes instructions 524 (such as software 522 on which is stored one or more sets of instructions 524 embodying any one or more of the methodologies or functions of staining mechanism 110 and staining architecture 120 as described with reference to FIG. 2 and other figures described herein) which operate in conjunction with processing logic 526 and processor 502 to perform the methodologies discussed herein.

Processor 502 represents one or more general-purpose processing devices such as a microprocessor, central processing unit, or the like. More particularly, the processor 502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 502 may also be one or more special-purpose processing devices such as an application specific integrated circuit (ASIC), a field programmable gate array (FPGA), a digital signal processor (DSP), network processor, or the like. Processor 502 is configured to execute the processing logic 526 for performing the operations and functionality of staining mechanism 110 and staining architecture 120 as described with reference to FIG. 2 and other figures discussed herein.

The computer system 500 may further include a network interface device 508, such as a network interface card (NIC). The computer system 500 also may include a user interface 510 (such as a video display unit, a liquid crystal display (LCD), or a cathode ray tube (CRT)), an alphanumeric input device 512 (e.g., a keyboard), a cursor control device 514 (e.g., a mouse), a signal generation device 540 (e.g., an integrated speaker), and other devices 516 like cameras, microphones, integrated speakers, etc. The computer system 500 may further include peripheral device 536 (e.g., wireless or wired communication devices, memory devices, storage devices, audio processing devices, video processing devices, display devices, etc.). The computer system 500 may further include a hardware-based application programming interface logging framework 534 capable of executing incoming requests for services and emitting execution data responsive to the fulfillment of such incoming requests.

Network interface device 508 may also include, for example, a wired network interface to communicate with remote devices via network cable 523, which may be, for example, an Ethernet cable, a coaxial cable, a fiber optic cable, a serial cable, a parallel cable, etc. Network interface device 508 may provide access to a LAN, for example, by conforming to IEEE 802.11b and/or IEEE 802.11g standards, and/or the wireless network interface may provide access to a personal area network, for example, by conforming to Bluetooth standards. Other wireless network interfaces and/or protocols, including previous and subsequent versions of the standards, may also be supported. In addition to, or instead of, communication via the wireless LAN standards, network interface device 508 may provide wireless communication using, for example, Time Division, Multiple Access (TDMA) protocols, Global Systems for Mobile Communications (GSM) protocols, Code Division, Multiple Access (CDMA) protocols, and/or any other type of wireless communications protocols.

The secondary memory 518 may include a machine-readable storage medium (or more specifically a machine-accessible storage medium) 531 on which is stored one or more sets of instructions (e.g., software 522) embodying any one or more of the methodologies or functions of staining mechanism 110 and staining architecture 120 as described with reference to FIG. 2 and other figures described herein. The software 522 may also reside, completely or at least partially, within the main memory 504, such as instructions 524, and/or within the processor 502 during execution thereof by the computer system 500, the main memory 504 and the processor 502 also constituting machine-readable storage media. The software 522 may further be transmitted or received over network 520 via the network interface card 508. Network 520 may be the same as network 270 of FIG. 2. The machine-readable storage medium 531 may include transitory or non-transitory machine-readable storage media.

Portions of various embodiments may be provided as a computer program product, which may include a computer-readable medium having stored thereon computer program instructions, which may be used to program a computer (or other electronic devices) to perform a process according to the embodiments. The machine-readable medium may include, but is not limited to, floppy diskettes, optical disks, compact disk read-only memory (CD-ROM), and magneto-optical disks, ROM, RAM, erasable programmable read-only memory (EPROM), electrically EPROM (EEPROM), magnet or optical cards, flash memory, or other type of media/machine-readable medium suitable for storing electronic instructions.

Modules 544 relating to and/or include components and other features described herein (for example in relation to staining mechanism 110 and staining architecture 120 as described with reference to FIG. 2) can be implemented as discrete hardware components or integrated in the functionality of hardware components such as ASICS, FPGAs, DSPs or similar devices. In addition, modules 544 can be implemented as firmware or functional circuitry within hardware devices. Further, modules 544 can be implemented in any combination hardware devices and software components.

The techniques shown in the figures can be implemented using code and data stored and executed on one or more electronic devices (e.g., an end station, a network element). Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals). In addition, such electronic devices typically include a set of one or more processors coupled to one or more other components, such as one or more storage devices (non-transitory machine-readable storage media), user input/output devices (e.g., a keyboard, a touchscreen, and/or a display), and network connections. The coupling of the set of processors and other components is typically through one or more busses and bridges (also termed as bus controllers). Thus, the storage device of a given electronic device typically stores code and/or data for execution on the set of one or more processors of that electronic device. Of course, one or more parts of an embodiment may be implemented using different combinations of software, firmware, and/or hardware.

Any of the above embodiments may be used alone or together with one another in any combination. Embodiments encompassed within this specification may also include embodiments that are only partially mentioned or alluded to or are not mentioned or alluded to at all in this brief summary or in the abstract. Although various embodiments may have been motivated by various deficiencies with the prior art, which may be discussed or alluded to in one or more places in the specification, the embodiments do not necessarily address any of these deficiencies. In other words, different embodiments may address different deficiencies that may be discussed in the specification. Some embodiments may only partially address some deficiencies or just one deficiency that may be discussed in the specification, and some embodiments may not address any of these deficiencies.

The following clauses and/or examples pertain to further embodiments or examples. Some embodiments pertain to Example 1 that includes an apparatus comprising: reception and processing logic to receive a request for a staining process for a specimen placed on a specimen container that is further placed within a process chamber, wherein the specimen includes a specimen needing a diagnosis; reading/capturing logic to read or capture process data relating to the specimen, wherein the process data includes at least one of basic information and customization instructions; and process control logic to facilitate the staining process of the specimen based on the process data.

Example 2 includes the subject matter of Example 1, further comprising a scanner or a barcode reader to read the basic information, wherein the basic information comprises basic data relating to one or more of the patient, a type of the specimen, a type of diagnosis or test, and a type of disease, wherein the basic information is read from a label on the specimen container, the label having a barcode, wherein the specimen includes one or more of a medical specimen, a chemical specimen, a biological specimen, a mechanical specimen, a physical specimen, wherein the medical specimen relating to a patient, wherein the medical specimen further includes a histological specimen including a microscopic anatomy of cells or tissues relating to one or more of humans, animals, and plants, wherein the specimen container includes one or more of a slide, a cassette, a test tube, and a flask.

Example 3 includes the subject matter of Example 2, further comprising a camera to capture the basic information from the label, wherein the camera is further to capture one or more features or changes to the one or more features of the specimen prior to, during, or after the staining process, wherein the one or more features include a size of the specimen, a color of the specimen, a reaction of the specimen at one or more stages of the staining process or in reaction to one or more formulation materials including one or more of chemicals, enzymes, water, and alcohol.

Example 4 includes the subject matter of Example 1, wherein the process control logic includes a hypo/hyper baric pressure module to facilitate, based on the process data, an osmotic process within the process chamber, wherein the osmotic process includes widening of pores of cell walls of the specimen to allow for the one or more formulation materials to enter the cell walls to intimately stain the specimen.

Example 5 includes the subject matter of Example 1, wherein the reception and processing logic is further to receive the customization instructions from a computing device over a network, wherein the customization instructions include the patient's doctor's preferences relating to the staining process, wherein the network comprises one or more of a cloud-based network, a Local Area Network (LAN), a Wide Area Network (WAN), a Metropolitan Area Network (MAN), a Personal Area Network (PAN), an intranet, an extranet, or the Internet.

Example 6 includes the subject matter of Example 5, wherein the customization instructions to instruct the process control logic to facilitate the staining process according the customization instructions, wherein the customization instructions further include a list of the one or more formulation materials to be extracted from a material reservoir to then be used for the staining process, wherein the material reservoir includes one or more stain vials for storing the formulation materials.

Example 7 includes the subject matter of Example 1, further comprising reiteration and recycling logic to reiterate or end the staining process based on the process data, wherein, if the staining process has ended, the reiteration and recycling logic is further to direct remaining formulation materials of the one or more formulation materials into a bio-hazard reservoir for an environmentally-friendly recycling of the remaining formulation materials.

Some embodiments pertain to Example 8 that includes a method comprising: receiving a request for a staining process for a specimen placed on a specimen container that is further placed within a process chamber, wherein the specimen includes a specimen requiring a diagnosis; reading or capturing process data relating to the specimen, wherein the process data includes at least one of basic information and customization instructions; and facilitating the staining process of the specimen based on the process data.

Example 9 includes the subject matter of Example 8, further comprising reading the basic information, wherein the basic information comprises basic data relating to one or more of the patient, a type of the specimen, a type of diagnosis or test, and a type of disease, wherein the basic information is read from a label on the specimen container, the label having a barcode, wherein the specimen includes one or more of a medical specimen, a chemical specimen, a biological specimen, a mechanical specimen, a physical specimen, wherein the medical specimen relating to a patient, wherein the medical specimen further includes a histological specimen including a microscopic anatomy of cells or tissues relating to one or more of humans, animals, and plants, wherein the specimen container includes one or more of a slide, a cassette, a test tube, and a flask.

Example 10 includes the subject matter of Example 9, further comprising capturing the basic information from the label, wherein capturing further includes capturing one or more features or changes to the one or more features of the specimen prior to, during, or after the staining process, wherein the one or more features include a size of the specimen, a color of the specimen, a reaction of the specimen at one or more stages of the staining process or in reaction to one or more formulation materials including one or more of chemicals, enzymes, water, and alcohol.

Example 11 includes the subject matter of Example 8, further comprising facilitating, based on the process data, an osmotic process within the process chamber, wherein the osmotic process includes widening of pores of cell walls of the specimen to allow for the one or more formulation materials to enter the cell walls to intimately stain the specimen.

Example 12 includes the subject matter of Example 8, further comprising receiving the customization instructions from a computing device over a network, wherein the customization instructions include the patient's doctor's preferences relating to the staining process, wherein the network comprises one or more of a cloud-based network, a Local Area Network (LAN), a Wide Area Network (WAN), a Metropolitan Area Network (MAN), a Personal Area Network (PAN), an intranet, an extranet, or the Internet.

Example 13 includes the subject matter of Example 12, wherein the customization instructions to facilitate the staining process according the customization instructions, wherein the customization instructions further include a list of the one or more formulation materials to be extracted from a material reservoir to then be used for the staining process, wherein the material reservoir includes one or more stain vials for storing the formulation materials.

Example 14 includes the subject matter of Example 8, further comprising reiterating or ending the staining process based on the process data, wherein, if the staining process has ended, the reiteration and recycling logic is further to direct remaining formulation materials of the one or more formulation materials into a bio-hazard reservoir for an environmentally-friendly recycling of the remaining formulation materials.

Example 15 includes at least one machine-readable medium comprising a plurality of instructions that in response to being executed on a computing device, causes the computing device to carry out operations according to any one of the aforementioned examples 8 to 14.

Example 16 includes at least one non-transitory or tangible machine-readable medium comprising a plurality of instructions that in response to being executed on a computing device, causes the computing device to carry out operations according to any one of the aforementioned examples 8 to 14.

Example 17 includes a system comprising a mechanism to carry out operations according to any one of the aforementioned examples 8 to 14.

Example 18 includes an apparatus comprising means to carry out operations according to any one of the aforementioned examples 8 to 14.

Example 19 includes a computing device arranged to carry out operations according to any one of the aforementioned examples 8 to 14.

Example 20 includes a communications device arranged to carry out operations according to any one of the aforementioned examples 8 to 14.

Some embodiments pertain to Example 21 includes a system comprising a storage device having instructions, and a processor to execute the instructions to facilitate a mechanism to perform one or more operations comprising: receiving a request for a staining process for a specimen placed on a specimen container that is further placed within a process chamber, wherein the specimen includes a specimen needing a diagnosis; reading or capturing process data relating to the specimen, wherein the process data includes at least one of basic information and customization instructions; and facilitating the staining process of the specimen based on the process data.

Example 22 includes the subject matter of Example 21, wherein the one or more operations further comprise reading the basic information, wherein the basic information comprises basic data relating to one or more of the patient, a type of the specimen, a type of diagnosis or test, and a type of disease, wherein the basic information is read from a label on the specimen container, the label having a barcode, wherein the specimen includes one or more of a medical specimen, a chemical specimen, a biological specimen, a mechanical specimen, a physical specimen, wherein the medical specimen relating to a patient, wherein the medical specimen further includes a histological specimen including a microscopic anatomy of cells or tissues relating to one or more of humans, animals, and plants, wherein the specimen container includes one or more of a slide, a cassette, a test tube, and a flask.

Example 23 includes the subject matter of Example 22, wherein the one or more operations further comprise capturing the basic information from the label, wherein capturing further includes capturing one or more features or changes to the one or more features of the specimen prior to, during, or after the staining process, wherein the one or more features include a size of the specimen, a color of the specimen, a reaction of the specimen at one or more stages of the staining process or in reaction to one or more formulation materials including one or more of chemicals, enzymes, water, and alcohol.

Example 24 includes the subject matter of Example 21, wherein the one or more operations further comprise facilitating, based on the process data, an osmotic process within the process chamber, wherein the osmotic process includes widening of pores of cell walls of the specimen to allow for the one or more formulation materials to enter the cell walls to intimately stain the specimen.

Example 25 includes the subject matter of Example 24, wherein the one or more operations further comprise receiving the customization instructions from a computing device over a network, wherein the customization instructions include the patient's doctor's preferences relating to the staining process, wherein the network comprises one or more of a cloud-based network, a Local Area Network (LAN), a Wide Area Network (WAN), a Metropolitan Area Network (MAN), a Personal Area Network (PAN), an intranet, an extranet, or the Internet.

Example 26 includes the subject matter of Example 25, wherein the customization instructions to facilitate the staining process according the customization instructions, wherein the customization instructions further include a list of the one or more formulation materials to be extracted from a material reservoir to then be used for the staining process, wherein the material reservoir includes one or more stain vials for storing the formulation materials.

Example 27 includes the subject matter of Example 21, wherein the one or more operations further comprise reiterating or ending the staining process based on the process data, wherein, if the staining process has ended, the reiteration and recycling logic is further to direct remaining formulation materials of the one or more formulation materials into a bio-hazard reservoir for an environmentally-friendly recycling of the remaining formulation materials.

Some embodiments pertain to Example 28 includes an apparatus comprising: means for receiving a request for a staining process for a specimen placed on a specimen container that is further placed within a process chamber, wherein the specimen includes a specimen needing a diagnosis; means for reading or capturing process data relating to the specimen, wherein the process data includes at least one of basic information and customization instructions; and means for facilitating the staining process of the specimen based on the process data.

Example 29 includes the subject matter of Example 28, further comprising means for reading the basic information, wherein the basic information comprises basic data relating to one or more of the patient, a type of the specimen, a type of diagnosis or test, and a type of disease, wherein the basic information is read from a label on the specimen container, the label having a barcode, wherein the specimen includes one or more of a medical specimen, a chemical specimen, a biological specimen, a mechanical specimen, a physical specimen, wherein the medical specimen relating to a patient, wherein the medical specimen further includes a histological specimen including a microscopic anatomy of cells or tissues relating to one or more of humans, animals, and plants, wherein the specimen container includes one or more of a slide, a cassette, a test tube, and a flask.

Example 30 includes the subject matter of Example 29, further comprising means for capturing the basic information from the label, wherein capturing further includes capturing one or more features or changes to the one or more features of the specimen prior to, during, or after the staining process, wherein the one or more features include a size of the specimen, a color of the specimen, a reaction of the specimen at one or more stages of the staining process or in reaction to one or more formulation materials including one or more of chemicals, enzymes, water, and alcohol.

Example 31 includes the subject matter of Example 28, further comprising means for facilitating, based on the process data, an osmotic process within the process chamber, wherein the osmotic process includes widening of pores of cell walls of the specimen to allow for the one or more formulation materials to enter the cell walls to intimately stain the specimen.

Example 32 includes the subject matter of Example 31, further comprising means for receiving the customization instructions from a computing device over a network, wherein the customization instructions include the patient's doctor's preferences relating to the staining process, wherein the network comprises one or more of a cloud-based network, a Local Area Network (LAN), a Wide Area Network (WAN), a Metropolitan Area Network (MAN), a Personal Area Network (PAN), an intranet, an extranet, or the Internet.

Example 33 includes the subject matter of Example 32, wherein the customization instructions to facilitate the staining process according the customization instructions, wherein the customization instructions further include a list of the one or more formulation materials to be extracted from a material reservoir to then be used for the staining process, wherein the material reservoir includes one or more stain vials for storing the formulation materials.

Example 34 includes the subject matter of Example 28, further comprising means for reiterating or ending the staining process based on the process data, wherein, if the staining process has ended, the reiteration and recycling logic is further to direct remaining formulation materials of the one or more formulation materials into a bio-hazard reservoir for an environmentally-friendly recycling of the remaining formulation materials.

While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements. It is to be understood that the above description is intended to be illustrative, and not restrictive.

What is claimed is:

1. An apparatus comprising:
a processing device coupled with memory, the processing device comprising:
reception and processing logic to receive a request for a staining process for a specimen placed in a specimen container that is further placed within a process chamber, wherein the request is received from a computing device that is communicatively part of a network and coupled to the apparatus;
reading/capturing logic to capture processing data relating to the staining process of the specimen, wherein the processing data is based on customization instructions received from the computing device, wherein the customization instructions to provide customization specifics for the staining process of the specimen, wherein the customization specifics to offer one or more of formulation materials, chemicals, enzymes, procedures, preferences, and pre-determined time periods for performing the procedures such that the staining process is performed in accordance with the customization specifics; and
process control logic to facilitate the staining process of the specimen based on the processing data, including the process control logic to control an atmospheric pressure within the process container.

2. The apparatus of claim 1, wherein the processing data is further based on basic information, wherein the basic information comprises essential specifics relating to one or more of a patient, a type of the specimen, a type of diagnosis or test, and a type of disease, wherein the basic information is read from a label on the specimen container, the label having a barcode, wherein the specimen includes one or more of a medical specimen, a chemical specimen, a biological specimen, a mechanical specimen, a physical specimen, wherein the medical specimen relating to the patient, wherein the medical specimen further includes a histological specimen including a microscopic anatomy of cells or tissues relating to one or more of humans, animals, and plants, wherein the specimen container includes one or more of a slide, a cassette, a test tube, and a flask.

3. The apparatus of claim 2, further comprising a camera to capture one or more of the basic information and the customization instructions from the label, wherein the camera is further to capture one or more features or changes to the one or more features of the specimen prior to, during, or after the staining process, wherein the one or more features include a size of the specimen, a color of the specimen, a reaction of the specimen at one or more stages of the staining process or in reaction to one or more formulation materials including one or more of the materials, the chemicals, the enzymes, water, and alcohol.

4. The apparatus of claim 1, wherein control of the atmospheric pressure within the process container by the process control logic includes control of a hypo/hyper baric pressure module to facilitate, based on the processing data, an osmotic process within the process chamber, wherein the osmotic process includes widening of pores of cell walls of the specimen to allow for the one or more formulation materials to enter the cell walls to intimately stain the specimen.

5. The apparatus of claim 4, wherein the process control logic to control the atmospheric pressure within the process container includes the process control logic to control one or more of a vacuum pump and a gas pump to reduce or increase the atmospheric pressure within the process container.

6. The apparatus of claim 1, wherein the network comprises one or more of a cloud-based network, a Local Area Network (LAN), a Wide Area Network (WAN), a Metropolitan Area Network (MAN), a Personal Area Network (PAN), an intranet, an extranet, or the Internet.

7. The apparatus of claim 6, wherein the customization instructions to instruct the process control logic to facilitate the staining process of the specimen in accordance with the customization specifics, wherein one or more of the formulation materials, the chemicals, and the enzymes are extracted from one or more material reservoirs, wherein the one or more material reservoirs include one or more stain vials for storing the one or more of the formulation materials, the chemicals, and the enzymes.

8. The apparatus of claim 1, further comprising reiteration and recycling logic to reiterate or end the staining process based on the processing data, wherein, if the staining process has ended, the reiteration and recycling logic is further to direct remainders of the one or more of the formulation materials, the chemicals, and the enzymes into a bio-hazard reservoir for an environmentally-friendly recycling of the remainders.

* * * * *